United States Patent [19]

Allison et al.

[11] Patent Number: 4,782,015
[45] Date of Patent: Nov. 1, 1988

[54] METHOD FOR DETERMING THE PRESENCE OF MALIGNANT CELLS

[75] Inventors: Anthony C. Allison, Belmont; Vera Morhenn, Palto Alto; Alain B. Schreiber, Mountain View, all of Calif.

[73] Assignee: Syntex (U.S.A.) Inc., Palo Alto, Calif.

[21] Appl. No.: 595,073

[22] Filed: Mar. 30, 1984

[51] Int. Cl.$^4$ .......................................... G01N 33/577
[52] U.S. Cl. .......................................... 435/7; 435/29; 435/810; 435/68; 435/172.2; 435/240.27; 935/106; 935/107; 935/108; 436/548; 436/813; 436/808; 530/387
[58] Field of Search ................ 935/106, 107, 108, 95; 436/548, 800, 536, 808, 501, 503, 813; 435/68, 172.2, 240, 241, 948, 43, 7.29, 240.27, 810; 260/112 R; 424/85, 86, 87; 128/630, 1, 1.1

[56]  References Cited
U.S. PATENT DOCUMENTS 4,361,544  11/1982  Goldenberg ............................ 424/1
4,443,427   4/1984  Reinhery et al. ..................... 424/1.1
4,448,890   5/1984  Smetana et al. ...................... 436/508

OTHER PUBLICATIONS

Tromovich et al., Arch Dermatal, vol. 110: 231-232 Aug. 1974.
Frederic E. Mohs, Archives of Surgery; vol. 42: 279-295, 1941.
Oseroff et al., Journal of Investigative Dermatology, vol. 84: 257-261, 1985.
Oseroff et al., Clinical Research, vol. 20 No. 2, 1982.
Morhenn et al., Journal of Investigative Dermatology, vol. 81; 127s-131s, 1983.
Suter et al., Journal of Immunological Methods, vol. 39, 407-411, 1980.

*Primary Examiner*—Christine M. Nucker
*Attorney, Agent, or Firm*—Theodore J. Leitereg

[57]  ABSTRACT

The present invention is concerned with a method for determining the presence of a malignant condition at a locus of interest. An exfoliative cell specimen obtained from the locus is contacted with an antibody specific for an antigenic site that is usually only found in the specimen when a malignant condition is present. The contact is made under conditions for detectable binding of the antibody to such antigenic site. After contact, the presence of binding of the antibody to the antigenic site is observed. The binding of the antibody is related to the presence of a malignant condition at the locus. The invention finds utility, for example, in the detection of cervical carcinoma.

10 Claims, No Drawings

METHOD FOR DETERMING THE PRESENCE OF MALIGNANT CELLS

BACKGROUND OF THE INVENTION

1. Field of the Invention

The examination of isolated cells or clumps of cells obtained by scraping or washing cut surfaces of tissues or mucous membranes has long proved a useful device in pathological examinations. Early detection of cervical cancer, achieved in part through screening of women with cytologic examination of a cervical Papanicolaou-type (PAP) smear, has contributed significantly to the major improvements in the management of this cancer during the last 30 years. Papanicolaou studied the cytologic examination of cervical smears in the 1940's and extended his initial observations in the early diagnosis of cancer of the human uterine cervix to many fields of cancer diagnosis.

Although the magnitude of benefit is controversial, it appears clear that routine screening of women at risk using the PAP smear is effective in preventing the invasive form of cervical cancer and mortality from it. The PAP smear has changed little since 1943 when Papanicolaou and Trout reported that the cellular changes that accompany malignant tumors of the female genital tract can be used in the early detection of cervical cancer. In the technique, a spatula is used to scrape the cervix, and the resulting exfoliated cells are smeared onto a microscope slide. These cells are stained using several staining steps, and then the exfoliated cells are examined for the presence of abnormal cells by a specially trained cytotechnologist. Examination of a single slide may take up to fifteen minutes. The cellular changes may clearly indicate a cancer or, more likely, may indicate abnormalities that may be due to early stages of a cancer or to inflammation due to some other cause such as an infection. The cellular changes associated with the early stages of cancer are the most difficult to interpret. For this reason it must also be emphasized that there should be careful correlation between the use of the PAP smear and classical biopsy methods.

The field of exfoliative cytology has been extended beyond vaginal, cervical, and endometrial uterine smears to bronchial and prostatic secretions, gastric and colonic washings, impressions of the surface of tumors or the cut surface of biopsy specimens, especially lymph nodes, and serous fluids.

Bronchial secretions such as sputum may be an important specimen for early detection of lung cancer. Lung cancer accounts for more than 25% of all cancer deaths, is the leading cause of cancer deaths in men and is becoming an increasingly serious problem in women. The incidence of lung cancer is increasing very rapidly, with an increase of sixfold over the last forty years. All of the factors that are suspected to contribute to the increased incidence of lung cancer are expected to continue to be a part of modern life so that early detection and effective treatment of lung cancer are essential if there is to be an impact on the mortality due to this disease. Only about 5% of lung cancer patients are cured. The low cure rate is due to a number of factors, a primary factor being that the cancer is often too widespread at the time of its diagnosis to be effectively treated. Most lung cancers are diagnosed on the basis of clinical symptoms such as cough, dyspnea (difficulty in breathing), chest pain, hemoptysis (blood in the sputum), and wheezing. Lung cancers are detected by physical examination, chest x-ray, or exfoliative cytology from a sputum specimen. The use of sputum cytology for early detection of lung cancer is controversial, and the American Cancer Society guidelines for early cancer detection do not recommend sputum cytology. However, other authorities believe that sputum cytology may be a method of early cancer detection. Many lung cancer patients shed cells that demonstrate increasing degrees of cytologic abnormality for long periods of time before the detection of obvious cancer. This disagreement as to the usefulness of sputum cytology is probably due to the lack of well-controlled studies, to variations in the preparation of the specimens for cytologic examination, and to variations in the interpretation of the cytologic changes.

2. Description of the Prior Art

A monoclonal antibody against human basal cells which affects the growth of epidermal cells in vitro is disclosed by Oseroff, et al., in *Clin. Res.*, 30:601A, 1982. Selective enrichment of human epidermal cell subpopulations using monoclonal antibodies is reported by Morhenn, et al., in *J. Inv. Derm.*, 81:127s–131s, 1983.

SUMMARY OF THE INVENTION

The present invention is concerned with a method for determining the likelihood of a malignant condition at a locus of interest in a mammalian host. The invention is based in part on the discovery that an exfoliative cell specimen obtained from the locus contains an antigenic site that is usually only present in the cell specimen during a malignant condition. The exfoliative cell specimen is contacted with an antibody specific for this antigenic site. The contact is carried out under conditions for detectable binding of the antibody to such antigenic site. The presence or absence of binding of the antibody to such antigenic site is observed and is related to the probability of a malignant condition at the locus.

The method of the invention finds utility in the detection of a malignant condition in the cervix, vagina, uterus, bronchus, prostate, gastro-intestinal tract including oral pharynx, mouth, etc., and exfoliative material aspirated from manifest tumors or cysts, the cut surface of biopsy specimens, especially lymph nodes, and serous fluids.

DESCRIPTION OF THE SPECIFIC EMBODIMENTS

The present invention provides for an improvement over the classical method of exfoliative cytology. In the method of the present invention, the presence of a malignant condition in an exfoliative cell specimen obtained from a locus of interest in a mammalian host is determined. By the term "exfoliative" is meant that the specimen comprises isolated cells or clumps of cells obtained by scraping or washing the surface of tissue, which cells are removed individually or in scales or laminae. The exfoliative cell specimen is to be distinguished from excised tissue such as that obtained by biopsy. The exfoliative cell specimen obtained from the locus is characterized in that a certain antigenic site is usually found in the specimen only when a malignant condition is present. In one embodiment this antigenic site shares determinants with an antigenic site of a normal cell that is not usually expected to be present in the exfoliative cell specimen. The specimen is contacted with an antibody that is specific for the aforementioned antigenic site. The antibody is capable of distinguishing over other cell types which are usually found in the specimen. Contact between the specimen and the antibody is made under conditions for binding of the antibody to the antigenic site. After contact, the presence or absence of binding of the antibody to the antigenic site is determined and is related to the presence of a malignant condition at the locus.

The invention will next be described in more detail using, for the purpose of illustration and not limitation, a monoclonal antibody that is specific for an antigenic site on a protein characteristic of human basal cells, both normal and malignant. Illustrative of such an antibody is a monoclonal antibody obtained from a murine hybridoma, which is designated VM-2. This VM-2 antibody is disclosed and claimed in patent application Ser. No. 595075 filed 3-30-84, entitled "Monoclonal Antibody Specific for Human Basal Cell Surface Antigen" filed on even date herewith. This monoclonal antibody is specific for an antigenic site on a protein characteristic of a human basal cell, both normal and malignant. The antigenic site is also found on malignant squamous cells and thus the antibody binds to malignant squamous cells. The protein has little, if any, associated lipid. When lysates of biosynthetically-labeled target cells are immunoprecipitated with VM-2 antibody and the precipitates are submitted to sodium dodecyl sulfate-polyacrylamide one-dimensional gel electrophoresis analysis (SDS-PAGE), the protein appears as a doublet (two bands) of molecular weight of about 120,000 daltons. The antibody is of the $IgG_1$ isotype. The VM-2 antibody does not bind to Staphylococcal Protein A at pH 7.3, nor does it bind to mesenchymal cells such as fibroblasts or endothelial cells. The VM-2 antibody is secreted by the VM-2 murine hybridoma.

Also useful in the method of the invention are fragments of the VM-2 monoclonal antibody such as Fab, F(ab')$_2$, Fv, and so forth. The antibody fragments are obtained by conventional techniques. For example, useful binding fragments may be prepared by peptidase digestion of the antibody using papain or pepsin.

A monoclonal antibody useful in the method of the invention may be produced according to the standard techniques of Köhler and Milstein, *Nature* 265:495–497, 1975. Conveniently, epidermal cells from psoriatic plaques are used as the immunogen. The psoriatic plaques are incubated and dispersed cells obtained. These cells are injected into a mouse, usually at two different points in time and, after a sufficient time, the mouse may be sacrificed and spleen cells obtained. The spleen cells are fused with myeloma cells or with lymphoma cells, generally in the presence of a non-ionic detergent, for example, polyethylene glycol. The resulting cells, which include the fused hybridomas, are allowed to grow in a selective medium, such as HAT-medium, and the surviving cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneum of a vertebrate host, which accepts the cells, and harvesting the ascites fluid. Where an insufficient amount of the monoclonal antibody collects in the ascites fluid, the antibody may be harvested from the blood of the host. Various conventional ways exist for isolation and purification of the monoclonal antibodies, so as to free the monoclonal antibodies from other proteins and other contaminants (see Köhler and Milstein supra).

While the VM-2 antibody is referred to above, this is by way of illustration and not limitation. Any antibody may be used if it binds to an antigenic site that is usually found in an exfoliative cell specimen only when a malignant condition exists and is capable of distinguishing over other cell types that are usually found in the specimen. Preferably, the antigenic site shares determinants with an antigenic site on a normal cell that is not usually expected to be present in the exfoliative cell specimen. The antibody may be from a murine source, a mammalian source including human, or other source, or a combination thereof. The antibody is preferably an IgG but may be an IgM, IgE, IgA, or the like.

In the method of the invention an exfoliative cell specimen is obtained from a locus of interest, i.e., a locus on or in a mammalian host, which locus may or may not have a malignant condition. The term "malignant condition" refers to the presence of displastic including carcinoma in situ, neoplastic, malignant or tumor cells or the like. The specimen may be obtained, for example, by scraping or washing of tissue at the locus. The locus may have membranes covered with squamous cells or with non-squamous cells. Depending on the nature of the tissue involved, or the location of the tissue as the case may be, one may collect an exfoliative body fluid, such as, for example, sputum, which body fluid has been in contact with, and may be said to have washed, the tissue at the locus. The exfoliative cell specimen may be obtained in accordance with the usual techniques of exfoliative cytology. In the detection of cervical carcinoma, for example, a scraping from the cervix would be taken. To determine the presence of malignancy in the lung, a sputum sample would provide the exfoliative cell specimen to be used in the present method.

The exfoliative cell specimen is next contacted with the aforementioned antibody under conditions for binding of the antibody to the specific antigenic site in the specimen to form antigen-antibody complexes. This antigenic site may be present on cells or cell fragments in the specimen. Generally, the specimen is placed on an appropriate support, such as, for example, a slide, usually glass, or some other suitable material. The exfoliative cell specimen is generally smeared on the slide to provide a thin layer of the specimen on the surface of the slide. The contact between the antibody and the specimen is generally carried out in an aqueous buffered medium. The buffers which may be employed include phosphate, tris, bicarbonate, etc. The pH is related to the nature of the specimen and the antibody, and is generally in the range of from about 5 to 8. The aqueous medium may additionally contain organic polar solvents in an amount of from about 0 to 40%. The organic polar solvents are water soluble and generally have from about 1 to 10 carbon atoms and from about 1 to 4 oxygen atoms. The antibody will be present in the aqueous medium at a concentration of about 1 to 100 µg/ml, preferably from about 10 to 20 µg/ml. The temperature during the contact of the specimen with the antibody is usually from about 4° to 40° C., preferably about 10° to 30° C. The period of contact is usually from about 15 to 120 minutes, preferably from about 30 to 60 minutes.

After the period of contact between the specimen and the antibody, the support is generally treated to remove unreacted antibody. Normally, this is accomplished by washing the support with an aqueous, usually buffered, medium. In general, the amount of wash solution should be sufficient to remove the unreacted antibody.

Next, the presence of binding of the antibody to the antigenic site in the specimen, which binding is related to the presence of a malignant condition at the locus, is observed. That is, the specimen is examined to determine the number of antigen-antibody (immune) complexes formed. It should be noted that in some instances very small numbers of the antigenic site in question may be found in the exfoliative cell specimen. However, in a malignant condition, large numbers of the antigenic site will be present and this latter condition is readily distinguishable by the present method over a non-malignant condition because a large number of antigen-antibody complexes will be measurable where a malignant condition exists. To make the determination of the presence of binding, means for producing a detectable signal is incorporated into the assay system. For example, one may conjugate the antibody employed in the assay to a label which is capable of producing a detectable signal. The label may be a radioactive entity, a chromophore including dyes and fluorescers, an enzyme, or the like. The number of labels employed for the antibody is generally determined by the requirements of the method of the present invention and the availability of sites for linking the label to the antibody. Methods for conjugating labels to antibodies and antibody fragments are well-known in the art. Such methods are exemplified in U.S. Pat. Nos. 4,220,450; 4,235,869; 3,935,074; 3,996,345; and 3,817,837.

Alternatively, one may contact the washed slide with a labeled specific binding partner for the antibody, which may be, for example, a labeled antibody specific for the antibody employed. Where the monoclonal antibody is derived from a murine source, a labeled anti-mouse immunoglobulin specific for the antibody employed in the method may be used. Such immunoglobulins may be raised according to standard techniques by injecting a suitable host with the monoclonal antibody, waiting for an appropriate time, and harvesting the anti-mouse immunoglobulins from the blood of the injected host. When a labeled specific binding partner for the antibody is employed, the slide must be washed again with an aqueous medium prior to examining the slide for fluorescence.

To determine the presence of binding between the antibody and the cell specimen where a fluorescer label is used, one may examine the slide for fluorescence, usually employing a fluorescence microscope. Where a label other than a fluorescer is employed, one may examine the slide or the specimen for the formation of a precipitate, a color, or the like.

The above description is directed primarily to an assay employing immunofluorescence techniques. However, the method of the invention may be practiced broadly within the immunoassay field. The assays may be homogeneous or heterogeneous. In a homogeneous assay approach, the exfoliative cell specimen is lysed and clarified to remove debris. The immunological reaction usually involves the specific antibody, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels which may be employed include free radicals, fluorescent dyes, enzymes, bacteriophages, coenzymes, and so forth.

In a heterogeneous assay approach, the reagents are usually the specimen, the specific antibody, and means for producing a detectable signal. The specimen is generally placed on a support, such as a plate or a slide, and contacted with the antibody in a liquid phase. The support is then separated from the liquid phase and either the support phase or the liquid phase is examined for a detectable signal employing means for producing such signal. The signal is related to the presence of the analyte in the specimen. Means for producing a detectable signal includes radioactive labels, fluorescers, enzymes, and so forth. Exemplary of heterogeneous immunoassays are the radioimmunoassay, immunofluorescence methods, enzyme-linked immunoassays, and the like.

For a more detailed discussion of the above immunoassay techniques, see "Enzyme-Immunoassay" by Edward T. Maggio, CRC Press, Inc., Boca Raton, Fla., 1980. See also, for example, U.S. Patent Nos. 3,690,834; 3,791,932; 3,817,837; 3,850,578; 3,853,987; 3,867,517; 3,901,654; 3,935,074; 3,984,533; 3,966,345; and 4,098,876, which listing is not intended to be exhaustive.

The invention also includes a diagnostic kit for carrying out the method disclosed above. The diagnostic kit comprises (1) means for obtaining an exfoliative cell specimen, e.g., a swab, and (2) a conjugate of a monoclonal antibody and a label, which conjugate is more specifically defined above. The conjugate reagent may also include ancillary agents such as buffering agents and protein stabilizing agents, e.g., polysaccharides and the like. The diagnostic kit may further include, where necessary, other members of the signal producing system of which system the label is a member, agents for reducing background interference in a test, control reagents, apparatus for conducting a test, e.g., a slide, and the like. In another embodiment, the diagnostic kit comprises (1) a monoclonal antibody more specifically defined above and (2) a conjugate of a specific binding partner of the above monoclonal antibody and a label capable of producing a detectible signal and (3) means for obtaining an exfoliative cell specimen. The kit may further include ancillary agents and, where necessary, other members of the signal producing system. The diagnostic kit may be employed alone or it may be used in conjunction with other tests, such as the standard PAP smear or with tests for other infections, such as, for example, chlamydia, herpes virus, gonorrhea, cytomegalovirus, and so forth.

EXAMPLES

The invention is further demonstrated by the following illustrative Examples. A number of procedures employed will be described first.

Cellular Enzyme Linked Immunosorbent Assay (ELISA)

(a) Cell lines: Human foreskin fibroblasts (HFF) were established from primary cultures derived from circumcisions; cells were used between transfers 4 to 10. Peripheral blood lymphocytes, mononuclear cells and erythrocytes were obtained from healty volunteers. The A-431 vulvar carcinoma cell line and A-549 bronchial carcinoma cell line and murine BALB/c 3T3 fibroblasts were obtained from Oncogen, Seattle, Wash. Hela cervical carcinoma cells, GH3 rat pituitary tumor cells, normal rat kidney fibroblasts (NRK), Daudi human B lymphoma, Molt T lymphoma and P388D1 murine macrophage cell line were obtained from the ATCC. Skin squamous cell carcinoma (SCC) cell line were obtained from Dr. N. Fusenig, Heidelberg, Germany, and bovine and rabbit aortic endothelial cells (EC) were prepared according to standard techniques. Bovine venous EC were obtained from the University of California at San Francisco and murine capillary EC from Dr. A. Curtis of Glasgow, Scotland. All tissue culture cells were grown in Dulbecco's Minimal Essential Medium (DMEM, MA Bioproducts) containing 10% fetal calf serum (Hyclone).

(b) Procedure: Adherent cells were grown to subconfluence in 96 well Linbro dishes; cells growing in suspension were allowed to adhere to the 96 well dishes for 30 min at 37° C. after precoating of the wells with 50 μl/well of a 0.1% poly L-lysine (Miles Laboratories) solution in phosphate buffered saline (PBS). Cells were then fixed in the wells for 5 min at room temperature with 0.25% glutaraldehyde (Sigma Chemical Corporation) and washed 3 times with PBS. Dishes were either used immediately or stored at 4° C. in humidified chambers. Cells were incubated at 37° C. for 2 hours (h) with monoclonal antibody, washed with PBS containing 0.1% bovine serum albumin (PBS-BSA) and further incubated with rabbit anti-mouse immunoglobulin (Ig) antibodies coupled to peroxidase (Zymed or Cappel) at 37° C. for 2 h. After washing with PBS-BSA, cells were incubated for 10 min at room temperature with 1 mg/ml ortho-phenylenediamine and 0.03% $H_2O_2$ in 0.1M citrate buffer pH 4.5. Optical density (O.D.) at 630 nm of individual wells was determined on a Dynatec ELISA plate reader. O.D. readings tenfold higher than that of controls (no first and/or no second antibody incubation) was considered to reflect significant binding of the antibody to the cell.

Immunofluorescence (IF) Staining of Frozen Section of Skin or Dispersed Cells The binding of antibodies to epidermal cells in situ was determined by IF using rabbit anti-mouse fluorescein isothiocyanate conjugated Ig (R/M-FITC). This reagent had been adsorbed on dispersed human skin cells. Frozen sections of skin were incubated with monoclonal antibody in humidified glass petri dishes for 15 minutes at room temperature, washed with phosphate buffered saline (PBS), labeled with R/M-FITC for 15 minutes and washed with PBS (Harrist & Mihm, 1979). Sections were covered with fluorescent antibody mounting fluid (DIFCO) and a glass coverslip and examined with a Zeiss fluorescence microscope. Trypsinized cell suspensions were labeled in a similar manner. Aliquots of labeled cells were resuspended in PBS, placed on a slide, covered with a glass cover slip and examined with a fluorescence microscope.

Immunoperoxidase (IP) Labeling of Frozen Skin Sections

Frozen sections of human skin were labeled using the immunoperoxidase staining technique (Rouse et al, 1978). Briefly, the tissue was fixed with acetone, incubated with antibody, washed with PBS, incubated with biotin-conjugated goat anti-mouse IgG (G/M-IgG)(Tago, Inc.), washed with PBS, labeled with avidin conjugated horseradish peroxidase, washed with PBS and $H_2O$, incubated with fresh diaminobenzidine solution and rinsed with PBS and $H_2O$. All incubations were at room temperature. The sections were processed in 0.5% $CuSO_4$ solution, counterstained with Giemsa, cleared and mounted. Slides were examined with a light microscope.

$^{35}S$-Methionine Labeling of VM-2 Antibody

Hybridoma cells producing VM-2 antibody were seeded into a microtiter well in methionine free DMEM containing 25 mM Hepes buffer, 4 mM L-glutamine, 4.5 gm/l glucose, 10 mM non-essential amino acids, 100 units/ml penicillin, 100 μg/ml streptomycin and 15% heat inactivated newborn calf serum (NCS). The cells were contacted for 6 hrs with 0.1 mCi $^{35}S$-methionine at 37° C., the supernatant removed and centrifuged to remove cells.

Isotype Determination of VM-2

(a) Ouchterlony immunodiffusion: An aliquot of supernatant of VM-2 hydridoma cells was placed into the center well of a 2% agar plate. Monospecific rabbit anti-mouse Ig isotype antibodies (Meloy) were placed in the outer wells and the plate was incubated for 2 h at room temperature and overnight at 4° C.

(b) Flexible polyvinylchloride 96 well plates (Costar) were coated with 0.1 mg/ml goat anti-mouse Ig antibodies for 2 h at 37° C. and countercoated with a 3% BSA solution for 2 h at 37° C. VM-2 hydridoma supernatant was then incubated at 37° C. for 2 h. After washing with PBS-BSA, plates were incubated at 37° C. for 2 h with monospecific rabbit anti-mouse Ig isotype antibodies coupled to peroxidase (Zymed). After washing, plates were incubated with 1 mg/ml ortho-phenylenediamine and 0.03% $H_2O_2$ in 0.1M citrate buffer pH 4.5. Optical density at 630 nm was determined on a Dynatec ELISA plate reader.

Staphylococcal Protein A Binding Assay

Microtiter wells were incubated with 5% NCS in PBS plus 0.02% $NaN_3$ and the supernatant was aspirated. Twenty-five μl of a suspension of epidermal cells ($2\times10^7$ cells/ml) were added to each well and incubated with 25 μl of VM-2 for 1 h at room temperature. The plates were centrifuged at 1200 rpm for 7 min, washed twice with 50% NCS/PBS $NaN_3$ and 25 μl of $^{125}I$-staphylococcal protein A (about 50,000 cpm/25 μl) were added. The plates were incubated for 1 h at 25° C., washed twice with 5% NCS/PBS $NaN_3$ and dried. The bottom of the wells were cut off and counted in a gamma counter.

Immunoprecipitation studies

SCC, A-431, Hela and HFF cells were grown to subconfluence in 100 mm tissue culture dishes in DMEM containing 10% FCS. Cells were incubated at 37° C. for 4 h with 100 μCi [$^{35}S$]-methionine in DMEM deficient in methionine (GIBCO) containing 1% dialyzed FCS. Cells were washed with PBS-BSA and lysed with PBS containing 0.5% Triton X-100 (Sigma) for 30 min. at 4° C. Lysates were centrifuged for 4 min. at 10,0000 xg in an Eppendorf centrifuge to remove cell nuclei and debris. Lysates were then incubated at 4° C. for 2 h with 20 μg VM-2 antibody and antigen-antibody complexes were precipitated with 100 μg goat anti-mouse Ig antibody by overnight incubation at 4° C. and centrifugation. Immunoprecipitates were washed 4 times with PBS-BSA containing 0.1% Triton X-100 and solubilized in 20 ml Laemli sample buffer by boiling for 2 min. Antigen analysis was performed on 5-15% acrylamide gradient one dimensional sodium dodecyl sulphate polyacrylamide slab gels. Gels were run at 30 mA constant intensity for 6 h, stained with Coomassie Brilliant Blue, destained, treated with Enhance ® (NEN), dried and processed for fluorography for one or two days. Borohydride tritiated protein mixtures were prepared using standard techniques and were run in parallel to allow apparent molecular weight determinations.

EXAMPLE 1

Preparation of VM-2 Antibody

A. Isolation and Culture of Human Epidermal Cells

Single cell suspensions of skin cells were prepared from split thickness skin from psoriatic plaques removed with a keratotome (Davol) preset at 0.015 inches or from skin obtained at surgery. Full thickness skin obtained at surgery was trimmed, cut into 1×5 mm strips and split-cut with a Castroviejo keratotome set at 0.1 mm. Strips of split-thickness skin were treated for 25 min at 537° C. with 0.3% trypsin (ICN Pharmaceuticals) in 0.8% NaCl, 0.04% KCl, 0.1% glucose, pH 7.3, plus 0.1% EDTA. The skin slices were washed, transferred to complete growth medium consisting of Dulbecco's Minimum Essential Medium (DMEM) plus 10% heat inactivated fetal calf serum (FCS), 50 µg/ml gentamicin, 2 mM L-glutamine, 50 units/ml penicillin, 50 µg/ml streptomycin and the basal and malpighian cells were released into the medium by gentle agitation. For culture, $2 \times 10^6$ viable, round refractile cells from normal skin were plated on a collagen thin gel coated 3.5 cm petri dish (Flow Labs) and incubated in 5% $CO_2$:95% air at 37° C. Viability was determined by trypan blue exclusion.

B. Production of Antibody

Using standard techniques (Köhler and Milstein, supra), MOPC-21 myeloma cells were fused with spleen cells obtained from a BALB/c(NIH strain)mouse. To immunize and boost the mouse, keratotome sections from psoriatic plaques from 2 unrelated donors were incubated in trypsin/EDTA as described above. The dispersed cells were washed once with complete growth medium, resuspended in PBS and injected into the mouse intraperitoneally. The antibodies produced by fused cells were screened by the immunofluorescence technique described above using frozen sections prepared from both normal skin and skin obtained from psoriatic plaques. Skin for frozen sections from psoriatic plaques was obtained using a local anesthetic and a 3 mm biopsy punch.

EXAMPLE 2

A. Characterization of VM-2 Antibody

VM-2 was cloned and then subcloned 2 times. The last two cultures were derived from microtiter wells for which serial dilutions predicted ½ cells/well. Cells were grown in large scale in 75 cm² tissue culture flasks for 12 h in the absence of fetal calf serum. Conditioned medium was precipitated with 35% saturated ammonium sulfate for 4 h at 4° C. Precipitates were extensively dialyzed against PBS and yielded 10-20 µg/ml medium semipurified VM-2 antibody. Alternatively, $10^7$ VM-2 cells were injected intraperitoneally in pristane treated BALB/c mice. After 10 days ascites fluid was collected, cleared by centrifugation and precipitated with 35% saturated ammonium sulfate. After dialysis, VM-2 antibody was further purified by gel chromatography on an LKB Ultragel AcA-34 column. Ascites fluid yielded between 2-5 mg antibody/ml. The $IgG_1$ nature of VM-2 was also confirmed by the solid phase double antibody ELISA procedure described above. On one dimensional gel electrophoresis, the antibody consists of two heavy chains of molecular weight of about 50,000 daltons, and two light chains of moleclar weight about 25,000 daltons. The antibody does not bind to staphylococcal protein A. On Ouchterlony immunodiffusion, a precipitin band was seen only in the area of the antibody against $\gamma_1$ and anti-7s antibody. Thus, VM-2 is an IgG of the $\gamma_1$ subtype.

VM-2 did not inhibit cellular growth. Cultures treated with a 1:10 dilution of VM-2 showed about a 4-fold increase in DNA content during the period of culture as did the controls.

VM-2 antibodies did not affect the growth of keratinocytes over a six-day period and did not inhibit growth of fibroblasts over a five-day period.

B. The specificity of VM-2 antibody was further assessed by cellular ELISA on various cell types as described above. Results are summarized in Table I. VM-2 binds to a determinant on an antigenic site present on SCC, A-431, A-549 and Hela cells. Normal fibroblasts, endothelial cells or cells from the hematopoietic lineage are not recognized by the VM-2 antibody.

C. Upon immunoprecipitation of the VM-2 antibody incubated with lysates of biosynthetically radioactively labeled target cells, 2 protein bands, each of apparent molecular weight of approximately 120,000 daltons, were revealed by fluorography. Protein bands of similar molecular weight were obtained from SCC, A-431 and Hela cells, although in different relative amounts. No protein was precipitated from control HFF cells under the same conditions.

TABLE I

Binding of VM-2 Antibody to Cells as Determined by Cellular ELISA

| Cell Type | Reactivity with VM-2 Antibody |
| --- | --- |
| Skin squamous cell carcinoma (human) | +++ |
| A-431, vulvar carcinoma (human) | ++ |
| A-549, bronchial carcinoma (human) | + |
| Hela, cervical carcinoma (human) | +++ |
| Foreskin fibroblasts (human) | — |
| 3T3 fibroblasts (murine) | — |
| Kidney fibroblasts (rat) | — |
| Peripheral blood lymphocytes (human) | — |
| Peripheral blood monocytes (human) | — |
| Erythrocytes (human) | — |
| MOLT, T lymphoma (human) | — |
| Daudi, B lymphoma (human) | — |
| P388 $D_1$, macrophages (murine) | — |
| Aortic endothelial cells (bovine, rabbit) | — |
| Venous endothelial cells (bovine, murine) | — |

At 10 µg/ml VM-2 antibody
+: O.D. > 10 times background
++: O.D. > 20 times background
+++: O.D. > 40 times background

EXAMPLE 3

Conjugation of VM-2 Antibody to Fluorescein

VM-2 antibody (5 mg/ml) was reacted with a tenfold molar excess of fluorescein isothiocyanate immobilized on Celite (Molecular Probes) for 30 minutes in the dark at room temperature in a 0.2M bicarbonate buffer, pH 9.2. Excess fluorescein isothiocyanate was removed by gel chromatography on a Sephadex G50 column in phosphate buffered saline. The fluorophore/protein ratio was calculated from the absorbance of the conjugate at 493 nm and 280 nm and varied between 2.4 to 4.2 from one preparation to another.

The antibody conjugates were either kept at 4° C. in the presence of 0.1% merthiolate or frozen in aliquots at −70° C. in the presence of 10% glycerol.

EXAMPLE 4

Determination of the Presence of Malignant Cells in Exfoliative Cell Specimens Obtained from the Cervix Cervical smears were obtained from 20 healthy volunteers on routine gynecological examination and from 20 patients with invasive squamous cervix carcinoma established independently by conventional cytology of biopsies. The smears were acetone dipped for 5 min at room temperature, air "dried" and kept desicated at −70° C. until use. The smears were then covered with 200 $\mu$l of 10–50 $\mu$g/ml fluoresceinated VM-2 antibody, prepared as described in Example 3, for 30 min at room temperature in a humidified chamber. The smears were extensively washed in PBS by transfer in several Coplin jars, mounted in 50% glycerol in PBS and observed with a Zeiss Universal fluorescence microscope. No cellular staining was observed for any of the smears obtained from the healthy volunteers. In smears of 20 out of 20 patients with invasive squamous cervix carcinoma an intense membrane fluorescence staining was observed on small round cells in the sample. Large squamous cervical cells with pycnotic nuclei were not stained, nor were erythrocytes and polymorphs found in most of the samples. For some patients, available duplicate smears were stained according to the conventional Papanicolaou technique. The small round cells stained by the VM-2 antibody were confirmed in these samples as possessing neoplastic features (altered nucleus/cytoplasmic ratio and basophilic, abnormal nuclei).

The cell line, designated VM-2, was deposited on Mar. 21, 1984 at the A.T.C.C. (American Type Culture Collection, 12301 Park Lawn Drive, Rockhill, Md. 20852 U.S.A.) and received accession number HB38530.

The invention has been described in detail with particular reference to the above embodments. It will be understood, however, that variations and modifications can be effected within the spirit and scope of the invention.

What is claimed is:

1. A method for determining the presence of a malignant condition in an exfoliative cell specimen obtained from a locus of interest, which method comprises
    (a) contacting an exfoliative cell specimen with a monoclonal antibody that binds to a protein antigenic site of a normal or malignant cell from a locus other than a locus of interest, said antibody being specific for an antigenic site characteristic of normal basal cells and said protein having a molecular weight of about 120,000 by one dimensional gel electrophoresis, said antigenic site being found in said specimen only when a malignant condition is present, said antibody being capable of distinguishing said antigenic site from other antigenic sites which are found in said specimen, under conditions for binding of said antibody to said antigenic site to form immune complexes, and
    (b) observing the presence of said immune complexes, the presence of said immune complexes being related to the presence of a malignant condition at said locus of interest.

2. The method of claim 1 wherein said antibody is an antibody obtained from a culture of a hybrid continuous cell line having the identifying characteristic of A.T.C.C. HB8530 or a binding fragment of said antibody.

3. A method for detecting the presence of neoplastic cells in an exfoliative cell specimen obtained from a locus of interest, which comprises
    (a) contacting an exfoliative cell specimen with a monoclonal antibody that binds to an antigenic site on a protein characteristic of a normal and malignant human basal cell and a malignant squamous cell under conditions for binding of said antibody to said antigenic site wherein said antibody is an antibody obtained from a culture of a hybrid continuous cell line having the identifying characteristics of A.T.C.C. HB8530 or a binding fragment of said antibody, and
    (b) observing the presence of binding of said antibody to said antigenic site, the binding of said antibody being related to the presence of neoplastic cells in said specimen.

4. A method for detecting a malignant condition in the cervix, which comprises
    (a) contacting an exfoliative cell specimen obtained from the cervix with an antibody which binds to a protein on an antigenic site of normal and malignant basal cells, said antigenic site being present in said cell specimen only when a malignant condition exists, said protein being characterized as having a molecular weight of about 120,000 daltons as determined by one dimensional gel electrophoresis, under conditions for binding of said antibody to said antigenic site and
    (b) observing the presence of binding of said antibody to said antigenic site, the binding of said antibody being related to the presence of a malignant condition in the cervix.

5. The method of claim 4 wherein said antibody is an antibody obtained from a culture of a hybrid continuous cell line having the identifying characteristics of A.T.C.C. HB8530 or a binding fragment of said antibody.

6. The method of claim 4 wherein the binding is determined by contacting said specimen with a conjugate of a label and a specific binding partner for said antibody, said label being capable of producing a detectable signal.

7. The method of claim 4 wherein said antibody is conjugated to a label capable of producing a detectable signal.

8. The method of claim 6 wherein said label is a fluorescer.

9. A diagnostic kit, comprising in packaged combination
    (a) a conjugate of (1) a label which is a member of a signal producing system and (2) a monoclonal antibody that binds to an antigenic site on a protein of a normal and a malignant basal cell, said antigenic site being found in an exfoliative cell specimen only when a malignant condition is present, wherein said antibody is an antibody obtained from a culture of a hybrid continuous cell line having the identifying characteristics of A.T.C.C. HB8530 or a binding fragment of said antibody, and
    (b) means for obtaining said exfoliative cell specimen.

10. A diagnostic kit, comprising in packaged combination (a) a monoclonal antibody that binds to an antigenic site on a protein of a normal and a malignant basal cell, said antigenic site being found in an exfoliative cell specimen only when a malignant condition is present, wherein said antibody is an antibody obtained from a culture of a hybrid continuous cell line having the identifying characteristics of A.T.C.C. HB8530 or a binding fragment of said antibody, a conjugate of (1) a specific binding partner of said monoclonal antibody of (2) a label which is a member of a signal producing system, and (c) means for obtaining said exfoliative cell specimen.

* * * * *